United States Patent
Wapner et al.

(10) Patent No.: US 6,867,854 B1
(45) Date of Patent: Mar. 15, 2005

(54) LIQUID TO SOLID ANGLE OF CONTACT MEASUREMENT

(75) Inventors: Phillip G. Wapner, Palmdale, CA (US); Wesley P. Hoffman, Palmdale, CA (US)

(73) Assignee: The United States of America as represented by the Secretary of the Air Force, Washington, DC (US)

( * ) Notice: Subject to any disclaimer, the term of this patent is extended or adjusted under 35 U.S.C. 154(b) by 265 days.

(21) Appl. No.: 10/335,660

(22) Filed: Jan. 2, 2003

Related U.S. Application Data

(60) Provisional application No. 60/344,062, filed on Jan. 2, 2002.

(51) Int. Cl.$^7$ .......................... G01C 21/06; G01N 13/00
(52) U.S. Cl. .......................... 356/150; 427/8; 73/64.48; 73/64.52
(58) Field of Search ................................ 356/150, 154, 356/138, 399; 73/64.52, 64.43, 64.48, 73; 118/710, 113, 715, 319; 427/8

(56) References Cited

U.S. PATENT DOCUMENTS

| | | |
|---|---|---|
| 4,688,938 A | 8/1987 | Demoulin et al. |
| 5,080,484 A | 1/1992 | Schneider et al. |
| 5,137,352 A | 8/1992 | Blitshteyn et al. |
| 5,143,744 A | 9/1992 | Barth et al. |
| 5,526,546 A | 6/1996 | Kamen |
| 5,708,506 A | 1/1998 | Birang |
| 5,792,941 A * | 8/1998 | Rye et al. .................. 73/53.01 |
| 5,815,256 A | 9/1998 | Fukunaga |
| 5,838,445 A | 11/1998 | Sandhu et al. |
| 5,861,946 A | 1/1999 | Hudson et al. |
| 6,221,955 B1 | 4/2001 | Mequanint et al. |
| 6,222,184 B1 | 4/2001 | Kinnunen |
| 6,280,883 B1 | 8/2001 | Lamanna et al. |
| 6,288,157 B1 | 9/2001 | Jariwala et al. |
| 6,291,022 B1 | 9/2001 | Hong et al. |
| 6,299,981 B1 | 10/2001 | Azzopardi et al. |
| 6,312,808 B1 | 11/2001 | Veerasamy et al. |
| 6,340,192 B2 | 1/2002 | Pike et al. |
| 6,353,051 B1 | 3/2002 | Huang |
| 6,368,664 B1 | 4/2002 | Veerasamy et al. |
| 6,370,947 B1 | 4/2002 | Casati et al. |

* cited by examiner

Primary Examiner—Gregory J. Toatley, Jr.
Assistant Examiner—Roy M. Punnoose
(74) Attorney, Agent, or Firm—Gerald B. Hollins; Fredric L. Sinder

(57) ABSTRACT

A liquid to solid material surface contact angle measurement system operating by way of detecting a transition in the behavior of a liquid sample with the solid material in a changing angular confinement environment along with use of a mathematical algorithm to then determine contact angle. Measurement of the angle at which the tested liquid transitions between apparent wetting and apparent non-wetting behavior, regardless of whether the liquid and solid material are truly classified as wetting or non-wetting, provides a measurement from which disclosed mathematical algorithms can predict the surface wetting characteristics of the liquid on the solid material. Automated performance of the confinement environment measurement and examples are included.

20 Claims, 8 Drawing Sheets

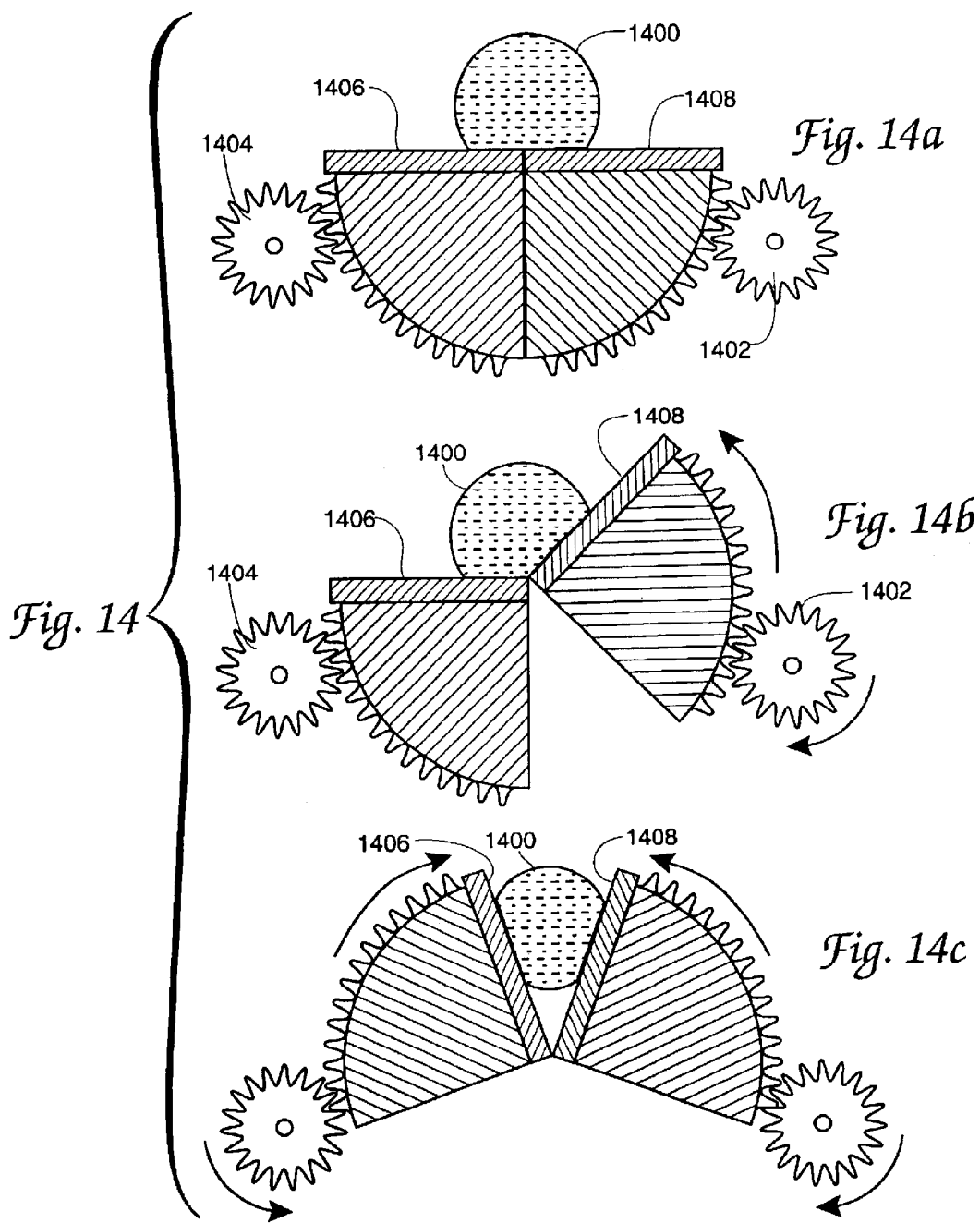

LIQUID TO SOLID ANGLE OF CONTACT MEASUREMENT

CROSS REFERENCE TO RELATED PATENT DOCUMENT

This application claims the benefit of U.S. Provisional Application No. 60/344,062, filed Jan. 2, 2002.

The present document is somewhat related to the commonly assigned, copending and filed of even date herewith patent document "Modification of Apparent Wettability of Solids With Liquids by Control of Surface and Micro-Channel Capillary Geometry", applicants' attorneys' docket number AFD 568, U.S. Patent and Trademark Office Ser. No. 10/340,381. The contents of this somewhat related application and all other documents referenced herein are hereby incorporated by reference herein.

RIGHTS OF THE GOVERNMENT

The invention described herein may be manufactured and used by or for the Government of the United States for all governmental purposes without the payment of any royalty.

BACKGROUND OF THE INVENTION

The wetting behavior of a liquid on a solid surface is a phenomenon of significant practical importance. The angle of liquid-to-solid contact is important in diverse areas of science and technology such as adhesion, adsorption, lubrication, catalysis, solid-liquid reaction kinetics, heat transfer, electrical conduction, and micro-fluidic devices. The angle of contact is one way to measure and assess the phenomenon of liquid wetting of a solid surface.

The contact angle of a liquid on a surface may be used to define to what extent, if any, a liquid will "wet" or contact a surface. Whenever a liquid contacts a solid surface, several different types of behavior can be exhibited. At one extreme, a drop of liquid contacting a solid surface will spread out until it forms a thin film on the surface. This is called total wetting and in this case the liquid has a contact angle of zero with the surface. At the other extreme, a drop of liquid will sit on the surface like a marble with minimal contact. This behavior is termed non-wetting and the liquid in this case forms a contact angle of 180° with the surface. For situations in between these extremes, a drop will be formed that makes a well-defined contact angle, $\theta$, with the surface. This is called partial wetting.

The static contact angle between a liquid and a smooth planar horizontal surface is commonly referred to as being the intrinsic contact angle. This contact angle is only dependent on the material properties of the liquid and the smooth horizontal planar surface. FIGS. 1a, 1b, and 1c in the drawings illustrate drops that exhibit different contact angles. FIG. 1a shows an intrinsic contact angle, $\theta$, between 0 degrees and 90 degrees, i.e., of about 45 degrees. FIG. 1b shows an intrinsic contact angle of about 90 degrees. FIG. 1c shows an intrinsic contact angle greater than 90 degrees but less than 180 degrees.

The apparent contact angle is the static contact angle between a liquid and a horizontal surface with contamination, imperfections, and/or roughness (with the roughness being on a scale that is small compared to the size of the drop). In contrast to both the intrinsic and apparent contact angle, the dynamic contact angle is measured on a drop that is changing size or position, and is not necessarily on a horizontal surface.

For all these different types of contact angles, the standard historical convention applied to the partial wetting behavior in FIG. 1 states that if the contact angle is less than 90 degrees, the liquid "wets" the surface. If the contact angle is greater than 90 degrees, the liquid "does not wet" the surface and is termed "non-wetting". In this application, the terms "wetting" and "non-wetting" will be used to refer to this partial wetting behavior and not to the absolute definitions.

Because the wettability of liquids on solid surface is important to quantify, there have been many approaches used to measure the contact angle of a liquid on a solid surface. Prior art measurement approaches have included the sessile drop method, the tilting plate method, the Wilhelmy plate method and the capillary rise method. Typically, the wettability of a surface is determined largely by the intrinsic contact angle, $\theta$, that the liquid makes with the solid surface. The tilting plate method may be difficult to perform if only small amounts of liquid are available. The other methods typically require expensive goniometer-mounted telemicroscopes to accurately view the contact angle optically. These techniques may also have difficulty measuring the contact angle, $\theta$, to an accuracy of better than 5 degrees. These techniques may also have difficulty measuring dynamic changes in the contact angle, $\theta$. In addition, some of these techniques require expensive computer software to analyze the liquid interface and obtain a desirable accuracy of one percent in the measurement of contact angle.

In the prior art, the contact angle that the liquid makes with the solid surface is determined directly in order to determine the wettability of a surface. In many cases this is very difficult to perform due to the size of the drop. In the present invention, the contact angle of a liquid with a surface or a portion of a surface is determined indirectly by observing whether the liquid is able to fill or not fill an angular feature having at least two opposing sides with a known included angle between them. This angular feature is fabricated from the material in question. This is much easier to accomplish than observing the contact angle directly.

With the expanded need in the scientific and technical community to measure the contact angle of liquids on various surfaces, there is a need for a rapid and inexpensive means to measure both the static and dynamic contact angles of liquids on solid surfaces to one percent accuracy that will be accessible to any size laboratory, institution, or business.

SUMMARY OF THE INVENTION

The present invention provides a measurement of liquid to solid material surface contact angle, $\theta$, on a surface, even if the surface is not planar or horizontal. This contact angle, $\theta$, provides a quantitative measure of surface wetting.

It is therefore an object of the present invention to provide a convenient measure of contact angles for various combinations of liquid and solid materials.

It is another object of the invention to provide contact angle measurements that are based on an angle of transition between differing behavior modes of a liquid sample in a solid material surface test apparatus.

It is another object of the invention to provide contact angle measurements based on the ability of a liquid sample to fill a crevice, pore, capillary, or interstice between two solid material samples in a test apparatus.

It is another object of the invention to provide a contact angle measurement that is based on differing "angle of transition" to contact angle mathematical relationships for wetting and non-wetting liquids on solid material surfaces.

It is another object of the invention to provide a contact angle measurement that is based on an automated measure of angle of transition between differing behavior modes of a liquid sample in a solid material surface test apparatus.

It is another object of the invention to provide a contact angle measurement that is based on a plurality of different ways of sensing the ability of a liquid sample to fill a crevice or interstice between two solid material samples in a test apparatus.

It is another object of the invention to provide a contact angle measurement that can be practiced with the aid of an inexpensive throw-away tool.

These and other objects of the invention will become apparent as the description of the representative embodiments proceeds.

These and other objects of the invention are achieved by a sample transition angle-based method of characterizing the contact angle wetting response of a test liquid on a solid material surface, one embodiment of said method comprising the steps of:

exposing a sample of said test liquid to a test apparatus having a pair of planar segments of said solid material, including test surfaces of said solid material, disposed in selectable, substantially closed-vertex, angular dispositions;

said substantially closed-vertex angular dispositions in said test fixture being selectable between angles of zero degrees and one hundred eighty degrees in angular size range;

changing said test fixture selectable angular disposition, within said zero degrees and one hundred eighty degrees range, until said test liquid sample incurs a transition in planar segments contact behavior;

measuring a planar segments angular disposition, within said zero degrees and one hundred eighty degrees selectable range, at which said transition in planar segments liquid contact behavior occurs;

determining, from said planar segments angular measurement and a selected algorithm of planar segments angle and liquid contact angle mathematical relationships, liquid to solid contact angle wetting response characteristics of said applied test liquid sample and said solid material surface.

BRIEF DESCRIPTION OF THE DRAWINGS

The accompanying drawings incorporated in and forming a part of the specification, illustrate several aspects of the present invention and together with the description serve to explain the principles of the invention. In the drawings:

FIG. 14a shows additional details of parts of the FIG. 4 apparatus in a first use position thereof.

FIG. 14b shows additional details of parts of the FIG. 4 apparatus in a second use position thereof.

FIG. 14c shows additional details of parts of the FIG. 4 apparatus in a third use position thereof.

DETAILED DESCRIPTION OF THE INVENTION

Figure 1A:
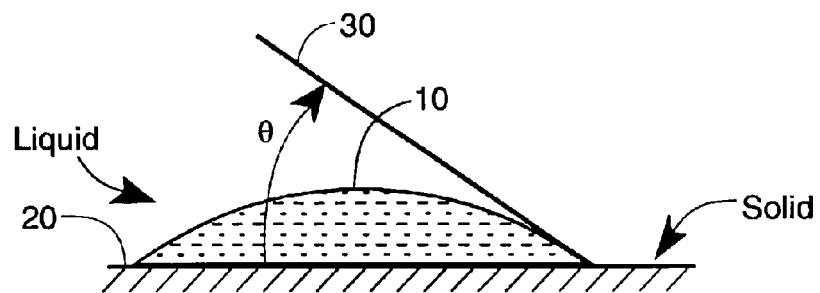
FIG. 1a shows a liquid to solid material intrinsic contact angle, $\theta$, that is between zero degrees and ninety degrees and is about forty-five degrees.
Figure 1B:
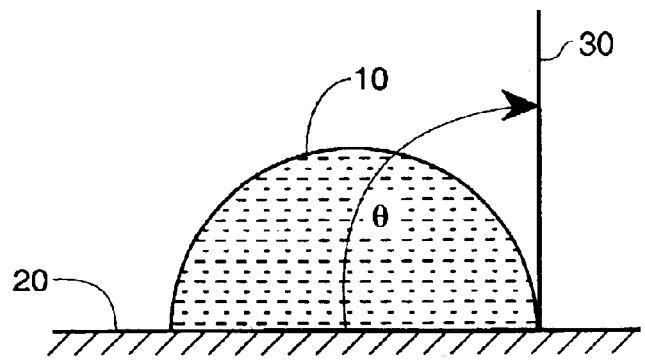
FIG. 1b shows a liquid to solid material intrinsic contact angle, $\theta$, that is about ninety degrees.
Figure 1C:
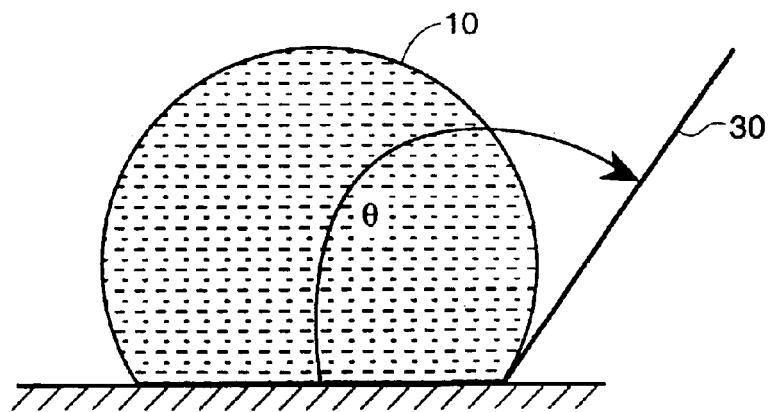
FIG. 1c shows a liquid to solid material intrinsic contact angle, $\theta$, that is greater than ninety degrees but less than one hundred eighty degrees.
Figure 3A:
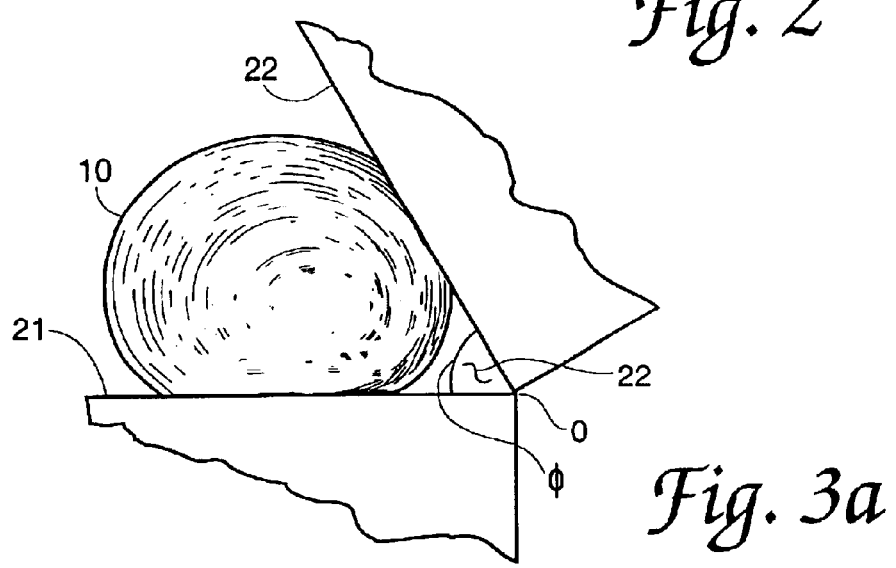
FIG. 3a shows a drop of mercury between plates forming about a sixty-degree angle.
Figure 3B:
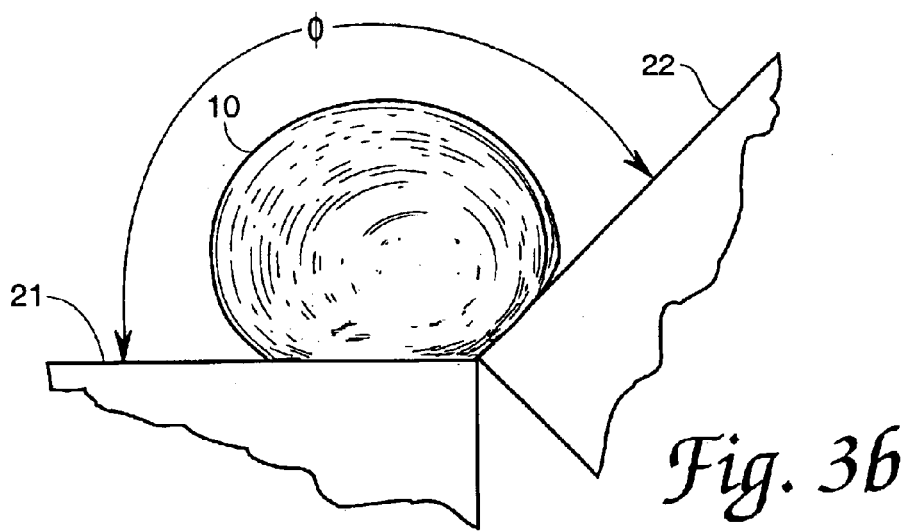
FIG. 3b shows a drop of mercury between plates forming about a one hundred thirty five-degree angle.

FIGS. 1a, 1b and 1c in the drawings show a drop of liquid 10, in contact with a solid surface 20. In each of FIGS. 1a, 1b and 1c the tangent line 30 indicates the angle $\theta$ formed between the liquid 10 and the solid surface 20 at the point of liquid contact with the surface. In the present invention whenever a non-wetting liquid 10 has contact angle, $\theta$, with the solid surface 20 that is greater than 90 degrees a relationship exists between angles formed between two apex-forming segments of that surface, segments forming an angle $\phi$ that determines whether or not complete liquid contact will take place within the included angle, $\phi$, formed by the two segments of the surface. In a similar manner whenever a wetting liquid has a contact angle, $\theta$, with a solid surface that is less than 90 degrees, a relationship exists between an angle $\phi$ formed between two segments of that surface that determines whether or not liquid will enter the included angle through the apex of the included angle, $\phi$, formed by the two segments. The respective subscripts "tnw" and "tw" may be added to the included angles, $\phi$, to segregate the non-wetting case transitional angle from the wetting case transitional angle. The terms "transitional included angle" and "transitional angle" "angle of transition", and "critical angle" as used herein may be regarded as making reference to the specific angle at which a liquid sample changes behavior between the apparent liquid wetting characteristics as shown in FIG. 3b and the apparent non-wetting liquid characteristics as shown in FIG. 3a. Similarly these same terms "transitional included angle", "transitional angle", "angle of transition", and "critical angle" may be regarded as referring to the specific angle at which a liquid sample changes behavior between the apparent non-wetting characteristics as shown in FIG. 3a and the apparent wetting characteristics shown in FIG. 3b.

In the prior art, the apparent wettability of a surface or a portion of a surface by a particular liquid is determined by the intrinsic contact angle, $\theta$, of the liquid acting in concert with surface properties such as contamination and surface roughness. In the present invention, the apparent wettability of a surface or a portion of a surface has been found to be determined by these same parameters which are also acting in concert with the localized surface non-planar features or specific capillary geometries. These non-planar features can take numerous forms, such as, intersecting plates, pits, pores, trenches, etc. The present inventors have found that there is a transitional included angle in these non-planar features or capillary geometries, for both wetting and non-wetting liquids, at which wetting behavior changes. For a non-wetting liquid this transitional included angle, $\phi$, is:

$$\phi_{tnw}=2\theta-180° \;(\theta \geq 90°) \qquad (1)$$

While for a "wetting" liquid the transitional included angle is:

$$\phi_{tw}=180°-2\theta \;(\theta \leq 90°) \qquad (2)$$

Where $\theta$ in each case is the contact angle that the liquid makes with the surface it is in contact with as shown in the views of FIG. 1.

Figure 2:
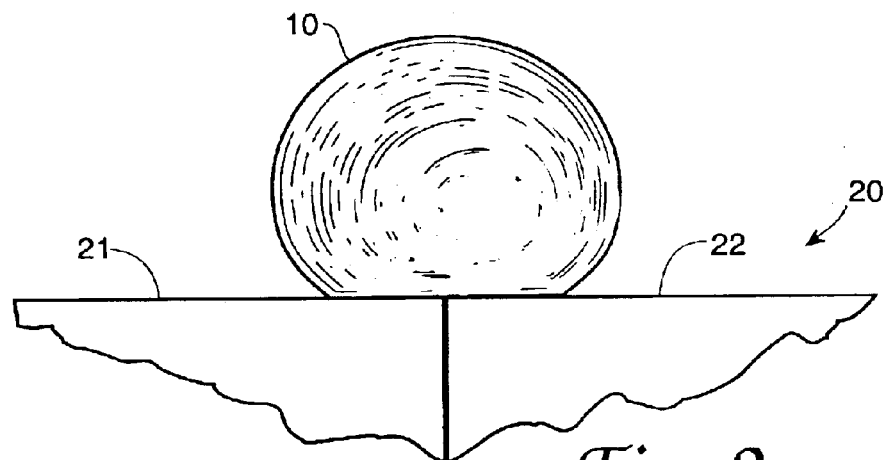
FIG. 2 shows a drop of mercury on a flat plate.

Consequently, for a non-wetting liquid, if the included angle, $\phi$, between the surfaces of pieces of material, between the portions of the surface features of a material, or between opposing walls of a capillary, is greater than $2\theta-180°$ the liquid will "wet" or completely contact the surfaces of the material that encompass the included angle $\phi$. This condition is shown in the drawings of FIG. 2 and FIG. 3b herein. If the included angle $\phi$ is less than this value, the liquid will not "wet" or completely contact the surface and will withdraw from the vertex region 23 of the included angle $\phi$ as is shown in the drawing of FIG. 3a.

The relationships in equations 1 and 2 can be used for determining the contact angle of a liquid with a particular solid. Thus, for a non-wetting liquid, equation 1 can be rearranged to solve for the contact angle giving equation 3.

$$\theta=(\phi_{tnw}+180°)/2 (\theta \geq 90°) \qquad (3)$$

In a similar manner, equation 2 can be arranged to solve for the contact angle of a wetting liquid giving equation 4.

$$\theta=(180°-\phi_{tw})/2(\theta \leq 90°) \qquad (4)$$

By determining the transitional included angle $\theta_t$ of a liquid with a surface, it is now possible to accurately calculate the contact angle of that liquid with the solid in question by using either equation 3 or 4. In FIG. 3 therefore experimentally testing or determining the transition angle $\theta_t$ at which the liquid 10 enters and does not enter the vertex O allows for the calculation of $\theta$.

Whenever a liquid has a contact angle, $\theta$, with a solid surface 20 that is greater than 90 degrees (a behavior usually referred to as non-wetting) a relationship exists between any angle, $\phi$, formed between two segments of that surface that determines whether or not complete contact will take place within the included angle, $\phi$, formed by the two segments. FIG. 3b shows a non-wetting liquid 10 placed at the intersection of the first plate 21 and the second plate 22 of the solid surface 20.

In the FIG. 2 and FIG. 3 examples, the non-wetting liquid may be mercury, a liquid that has a contact angle of 140° (FIG. 2) with the surface such as the glass plates on which it rests. The two flat plates in this FIG. 2 and FIG. 3 apparatus, can be rotated to any angle between 0 degrees and 180 degrees i.e., through the range of acute and obtuse angles (or substantially obtuse angles, such as angles one degree less than 180° for example). As can be seen, at an included angle of 60° (FIG. 3a), a non-wetting liquid is excluded from the intersection of the two plates 21 and 22 (i.e., from the interstice region between the two plates). However, when the included angle is increase to 135° as in FIG. 3b, the non-wetting liquid fills the interstice formed by the two plates. Clearly there is a change in the behavior of the liquid as the FIG. 3 included angle between the plates is varied from 60° to 135°. The present inventors have determined theoretically and confirmed experimentally that there is a transitional included angle, $\phi_{tnw}$, at which the behavior of the non-wetting liquid changes. Below this transitional included angle $\phi_{tnw}$ are angles where the non-wetting liquid withdraws from the interstice and no longer completely contacts the two segments at the intersection. Conversely while the plates are at an angle above this transitional included angle $\phi_{tnw}$ the liquid fills the interstice between the two plates.

Figure 4:
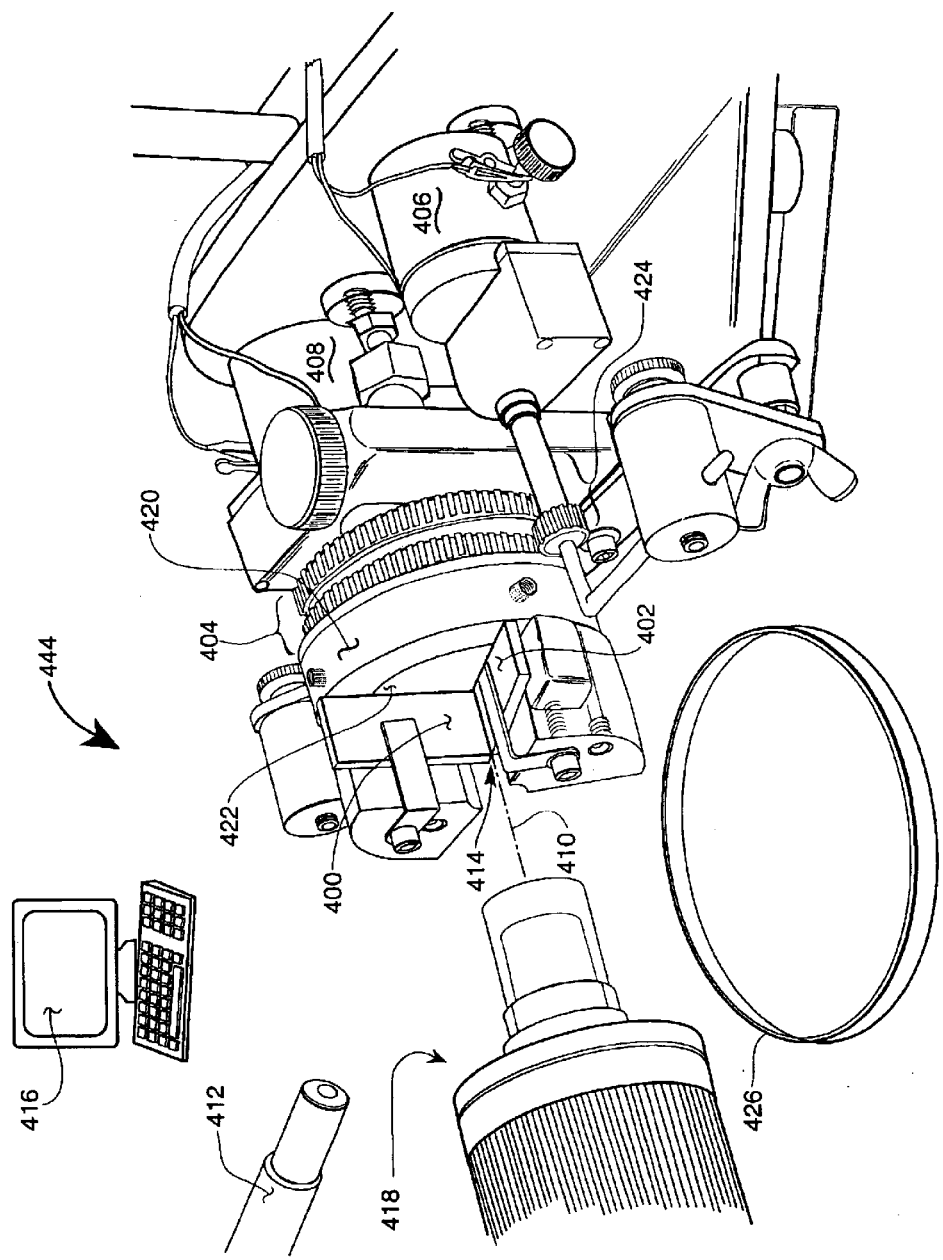
FIG. 4 shows one embodiment of an automated measurement apparatus according to the present invention.

It should be noted here that, although the plates in FIGS. 2–4 are shown as planar with the plates in contact at the interstice, this is not necessary. If the plates are not planar it is more difficult but not impossible to determine the included angle. If the plates are not in intimate contact at the interstice, the only requirement is that the gap between the edges of the plates at the interstice not be great enough to allow the non-wetting drop to pass through.

The relationship between the transitional included angle and the contact angle, $\theta$, that a non-wetting liquid makes with the surface that it is in contact with is in accordance with the above equation 1:

$$\phi_{tnw}=2\theta-180° \;(\theta \geq 90°) \qquad (1)$$

Substituting the value of the contact angle for mercury on glass into this equation gives a transitional included angle of 100°, which agrees with the experimental value determine by the apparatus.

By rearranging equation 1, one obtains the above equation 3:

$$\theta=(\phi_{tnw}+180°)/2 \;(\theta \geq 90°) \qquad (3)$$

Equation 3 shows that the contact angle of a non-wetting liquid can be easily calculated once the transitional included angle for the liquid on the desired surface is known. This transitional included angle is, of course, easily determined by observing the included angle at which the liquid will either enter or exit an interstice as described in the examples that follow.

Figure 5:
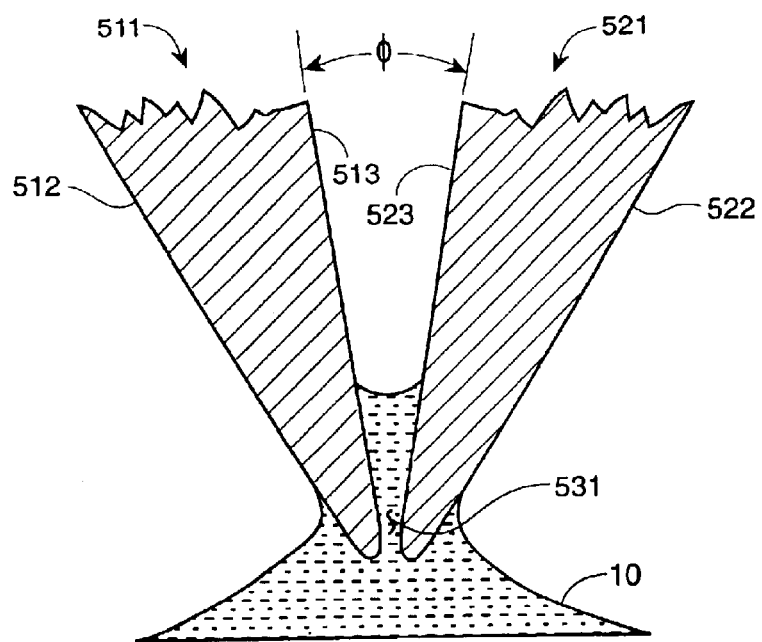
FIG. 5 shows a wetting liquid in an interstice of about fifteen-degrees with capillary wicking.

In a similar manner the transitional included angle for a wetting liquid, $\phi_{tw}$, is deduced theoretically and confirmed experimentally using a FIG. 5 first plate 511 and a second plate 521 of material that again form an included angle $\phi$. Each of the plates 511 and 521 include outside portions 512 and 522 and inside portions 513 and 523 respectively. At or near the vertex formed by the plates 511 and 512 is an interstice region 531. In this FIG. 5 case since the wetting liquid 10 will spontaneously fill the interstice 531, the plates are assembled in a "V" shape and the interstice placed in contact with the wetting fluid 10. It should be noted in FIGS. 5 and 6 that, although the plates are shown tapered, they can be of uniform thickness. Since it is the included angle between the inner surfaces, 513 and 523, that determines whether liquid will enter the apex, the shape of the plates is not critical. In addition, the separation of the plates at the apex is not critical within limits. That is, there needs to be at least a microscopic gap to admit liquid but if the space is too big, the liquid will not wick into the apex.

The maximum size of the gap for which this behavior applies is governed by the surface tension. Thus, by moving the plates apart until wicking stops, this invention can also be employed to measure surface tension. This also applies when intrinsic contact angles greater than 90° are being measured. The relationship between maximum gap size and surface tension is governed by Laplace's law of capillary action.

Figure 6:
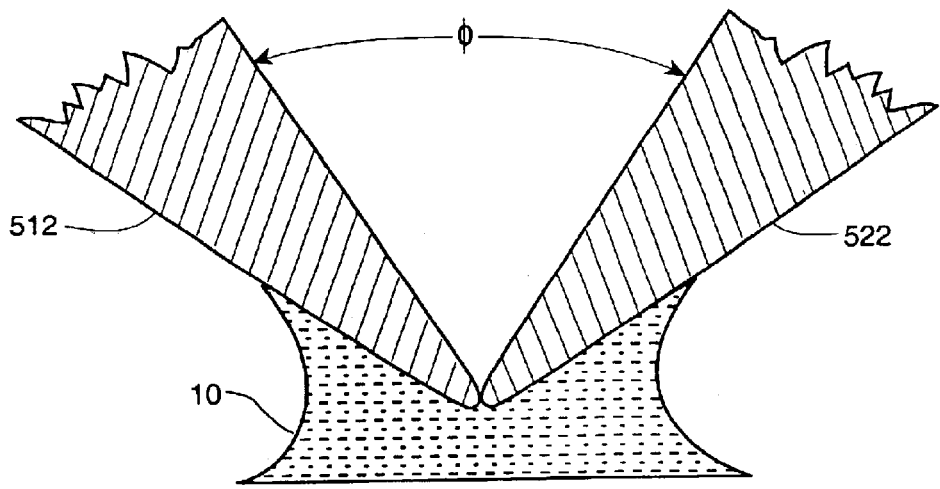
FIG. 6 shows a wetting liquid in an interstice of about forty-five degrees.

In FIG. 5 it can be observed that with an included angle φ of about 15° not only does the wetting liquid wick up the outside portions 512 and 522 of the plates but it enters the interstice 531 and rises up on the inside portions 513 and 523 between the plates. In contrast, when the included angle φ is about 45° as seen in FIG. 6, the wetting liquid 10 does not enter the interstice although it does wet the outside portions 512 and 522 of the "V". It is found theoretically that the transitional included angle for a wetting liquid, $\phi_{tw}$, is in accordance with the above equation 2:

$$\phi_{tw} = 180° - 2\theta \, (\theta \leq 90°) \tag{2}$$

In the example shown in FIG. 5 and FIG. 6, the plates may be made from Plexiglass® and the wetting liquid can be water which forms a contact angle of 75° with this surface. Thus, equation 2 would predict a transitional included angle of 30°, which is observed. As shown in FIG. 5 and FIG. 6 if the included angle φ is less than the transitional angle $\phi_{tw}$, filling of the included angle will occur by capillary action. As with non-wetting fluids it is not only the contact angle that determines whether a wetting fluid will fill an interstice but also the value of the included angle.

As in the case of non-wetting liquids, equation 2 can be re-arranged so that the contact angle θ between a wetting liquid and a surface may easily be determined by measuring the transitional included angle $\phi_{tw}$. Rearranging equation 2 gives:

$$\theta = (180° - \phi_{tw})/2 \, (\theta \leq 90°) \tag{4}$$

Equations 3 and 4 provide a basis for considering several examples that additionally clarify the nature of the present invention.

EXAMPLE 1

An apparatus similar to that shown in FIG. 4 can be used to measure the contact angle of a non-wetting liquid on a solid surface. In this apparatus, the surface of interest can be the plate itself, a coating on the plate surface, or a piece of film mounted to the plate surface. An apparatus of this type can be very simple and inexpensive or as sophisticated as desired. Instruments of this type share common features however. For example, they are active in the sense that actual motion of the plates allows observation of the withdrawal of liquid from or the entrance of the liquid into the interstice formed by the plates.

Figure 7A:
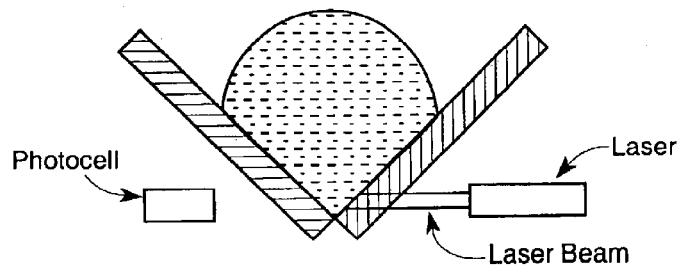
FIG. 7a shows light blocked from reaching a photocell by a liquid sample-filled interstice.
Figure 7B:
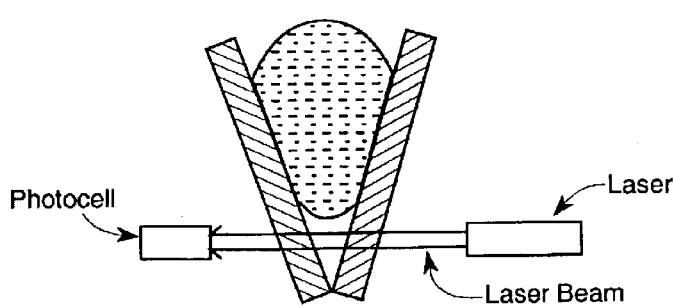
FIG. 7b shows light reaching a photocell by way of a liquid sample-voided interstice.

This movement can be observed visually, using appropriate optical means such as a video microscope. Alternately this movement can be discerned using other sensing techniques, such as a laser beam aimed into the interstice formed by the plates and impinging upon a photocell placed opposite the laser beam as is shown in FIG. 7 of the drawings herein. When the FIG. 7 drop fills the interstice, no laser light reaches the photocell. When the drop exits the interstice, the photocell becomes activated. It should be noted that FIG. 7 is drawn with the laser beam perpendicular to the interstice for the sake of drawing clarity. However, the laser beam can be disposed at any angle with respect to the interstice with a preferred angle being parallel to the interstice. Once movement of the droplet has occurred, the angle of the interstice formed by the plates can then be measured. Again this can either be accomplished optically with a device such as a goniometer, or by some other system capable of measuring angular displacements of the plates.

Figure 7C:
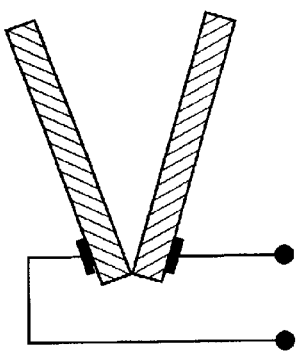
FIG. 7c shows electrical capacitance sensing of liquid sample presence in an interstice region.

Other types of systems for determining when the drop enters or begins withdrawing from the interstice include electrical techniques such as resistance, capacitance, and magnetic or inductive measurements. An electrical capacitance arrangement for such sensing is shown in FIG. 7c of the drawings; the two capacitance plates in this view may be connected to an alternating current capacitance bridge for example. These, and other related methods for measuring drop entrance or withdrawal, may need to be tailored to embrace the liquid properties of the drop as well as those of the surface. If the liquid is transparent to normal visual wavelengths, for example, then an infrared or ultraviolet laser is appropriately employed. Similarly, electrical resistance measurements are feasible if the liquid has readily measurable conductance as exists in the cases of mercury and acids for examples.

Clearly, surfaces of the "V" that the test sample droplet is exposed to can be different than the glass plates identified herein. The test sample drop can in fact be placed on the surfaces of plates made from virtually any solid material that can be formed into a plate. In addition a film of the desired material can be placed on the plates or any other material can be coated on the surface of the plates. Typical possible processes for applying such a coating include, but are not limited to, painting with a brush, spraying, electro-deposition, electroless-deposition, chemical-vapor deposition (CVD), and magnetron sputtering.

The non-wetting liquid droplet can be deposited into the interstice formed by the plates using a pipette or syringe, condensation from a vapor, or any other means of forming an appropriate size drop. Because withdrawal of the drop from the corner is both reproducible and reversible, the drop can be deposited into the corner formed by the plates with the corner, or included, angle being between 0 degrees and 180 degrees. If the included angle is small, meaning that it is lower than the critical included angle, $\phi_{mw}$, the plates of the apparatus may need to rotate away from one another increasing the included angle. When the critical included angle is reached, the drop completely fills the corner thereby measuring the contact angle of the liquid droplet with the solid plate. If the included angle is large, meaning that it is greater then the critical included angle, $\phi_{mw}$, the plates need to be rotated towards each other decreasing the included angle. When the critical included angle is then reached, the drop withdraws from the corner or interstice, again measuring the contact angle, θ, of the liquid droplet with the solid plates. The drop can be removed from the apparatus after the critical angle has been measured by any one of a variety of means. The simplest methods are tilting the apparatus or blowing air into the interstice formed by the plates.

It should be noted here that the speed with which the plates are rotated, either towards or away from one another, can influence the observed critical included angle, $\phi_{mw}$, and thus the contact angle, θ, measurement itself. This is not a fault of this measurement technique, but rather, a property of many liquids. Other contact angle measurement techniques, such as the sessile drop, Wilhelmy plate, and capillary rise techniques have demonstrated that some liquids exhibit dynamic, or moving liquid contact angles, $\theta_d$, that are different than the static, or non-moving liquid contact angles. The present invention apparatus is capable of measuring these dynamic contact angles simply by changing the rotation speed of the plates. This type of dynamic measurement is not so easily performed with some techniques of the prior art.

As stated above, present invention apparatus can be as sophisticated or inexpensive as desired. For a simple version of the apparatus that is portable, manual positioning of the plates can be accomplished with micrometer screws, the included angle, $\phi$, can be determined by a protractor type of scale, and the position of the drop can be determined by an inexpensive diode laser in conjunction with a battery powered detector. The apparatus shown in the FIG. 4 drawing herein provides convenience over this simple version and is somewhat more complex as is described below.

In the FIG. 4 measurement apparatus 444 a pair of angularly disposable measuring plates 400 and 402, of material to be tested for liquid contact angle characteristics, are mounted for controllable angular disposition on a pair of concentric tubes 420 and 422 centered on the horizontal axis 410. Each of the concentric tubes 420 and 422 and thus the plates 400 and 402 is controllable in angular orientation around a horizontal axis 410 by one of the electrical stepping motors shown at 406 and 408 and the associated gear trains represented at 424. The gear-coupled stepping motors provide small increments of angular change for plates 400 and 402 (i.e., angular increments of one-half or one degree are preferred) together with indefinite retention of attained plate positions. The measuring plates 400 and 402 in the FIG. 4 apparatus are each made of a material presumed to be optically transparent to radiant energy of some selected spectral frequency. This transparency enables use of the optical form of interstice angle liquid sample behavior detection described in connection with the FIG. 7a and FIG. 7b drawings; a light source usable for this purpose is shown at 412 in the FIG. 4 drawing. This light source is directed across the interstice region 414 of the plates 400 and 402 and provides illumination enabling operator use of the long focal length telescope 418 to observe liquid sample behavior in the interstice 414.

Electrical signals that may originate in a photo detector associated with the FIG. 4 apparatus can be used to automatically control a cycle of measuring plate angular dispositions appropriate for the liquid being tested if desired. Such control as well as storage of test results data may for example be accomplished with use of a suitably programmed computer of the personal computer type as is represented at 416 in the FIG. 4 drawing. Electrical detection of sample behavior in the angular interstice region between plates 400 and 402 may of course be used in the FIG. 4 apparatus when the solid material or the liquid under test is not optically transparent but have suitable electrical properties. Visual observation by a human operator, using the telescope 418 for example, can of course be used with many of the liquids and solid material combinations not amenable to either of the optical or electrical interstice sensing arrangements.

Liquid sample introduction into the apparatus 444 may be accomplished in the FIG. 4 arrangement by way of a pipette or other of the sample introduction arrangements described herein. Collection of liquid sample material passing through the angular interstice region between plates 400 and 402 may be accomplished with a beaker or other open container 426. This same container may be used to collect residue material remaining on the plates 400 and 402 upon completion of a test with the aid of compressed air or other plate cleaning mechanisms. The FIG. 4 test apparatus is of course suitable for measurement of either non-wetting or wetting characteristics between plates 400 and 402 and the test sample liquid.

Additional details of the FIG. 4 apparatus may perhaps be better understood from the working relationships shown in the three views of the FIG. 14 drawings herein. In FIG. 14a the plates 400 and 402 are identified with the numbers 1406 and 1408 (in view of the different plate shapes and sizes shown in the FIG. 14 views) and are shown disposed in a planar surface configuration. Energization of the stepping motors 406 and 408 in the FIG. 4 drawing provides rotation of the right and left hand drive gears 1402 and 1404 in the FIG. 14 apparatus and thereby moves the planer disposed plates 1406 and 1408 in FIG. 14a to one of the positions shown in FIG. 14b or FIG. 14c or some intermediate position as is dictated by the materials of the drop 1400 and plates 1406 and 1408 and their wetting characteristics. In FIG. 14b the drop 140 is shown in a fully contacting condition with the plates 1406 and 1408 while in FIG. 14c the drop is shown in an expelled condition with respect to the vertex intersection or interstice of plates 1406 and 1408. The drive gears 1402 and 1404 in the FIG. 14 drawing are located in different but parallel planes as may be appreciated from the FIG. 4 drawing. Notably the FIG. 4 and FIG. 14 apparatus provides symmetrical dispositions of the plates 400–1408 and 402–1406 with respect to the gravitational vector in order to determine if there was any effect of gravitational pull and other undesired effects on the drop 1400. None was observed for small drops. Thus, for small drops the plates don't have to be symmetrical. An example can be seen in FIG. 3.

EXAMPLE 2

Figure 8:
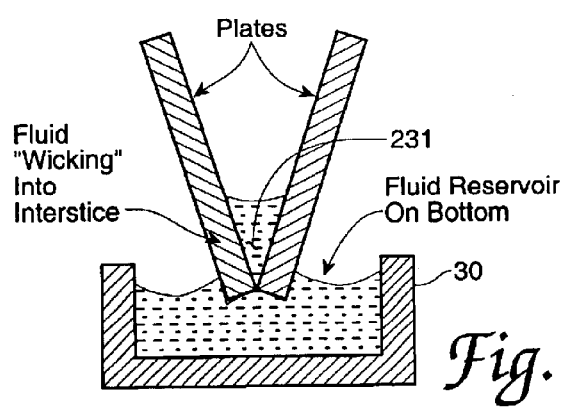
FIG. 8 shows a bottom-contacting sample liquid reservoir with included angle plates disposed at less than a sample transition angle.
Figure 9:
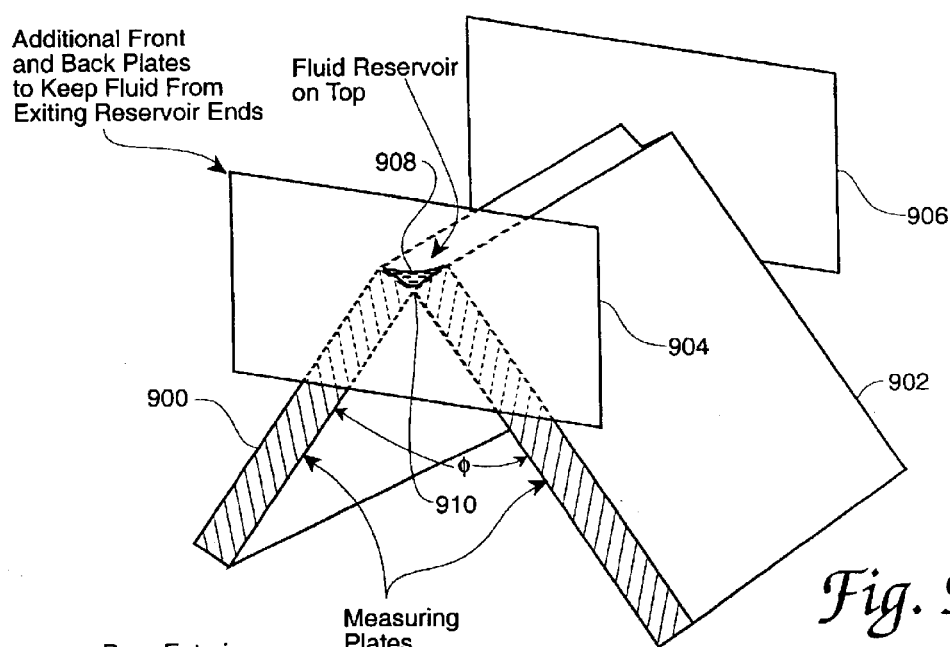
FIG. 9 shows a top-contacting sample liquid reservoir with included angle plates disposed at greater than a sample transition angle.

To determine the contact angle, $\theta$, of a wetting liquid 10 on a solid surface 20 the apparatus 444 in FIG. 4 can be used with a small reservoir 30 to bring the liquid of interest in contact with the exterior portion of the interstice as is shown in the essential elements representation of FIG. 8 of the drawings. Alternatively, the measuring apparatus 444 can be inverted so that the liquid 10 can be placed at the intersection of the plates on the external edge surfaces of the plates as appears in FIG. 9 of the drawings. In this FIG. 9 representation, two additional plates, 904 and 906, plates located orthogonally at each end of the interstice 910, may be brought into endwise contact with the measuring plates 900 and 902 forming the included angle, $\phi$, to prevent the liquid 908 from running off of the intersection of the measuring plates. In FIG. 9 the liquid 908 is shown as being excluded from the interstice 910 because the included angle, $\phi$, is shown to be greater than the transitional included angle, $\phi_{tw}$, in size.

EXAMPLE 3

Figure 10:
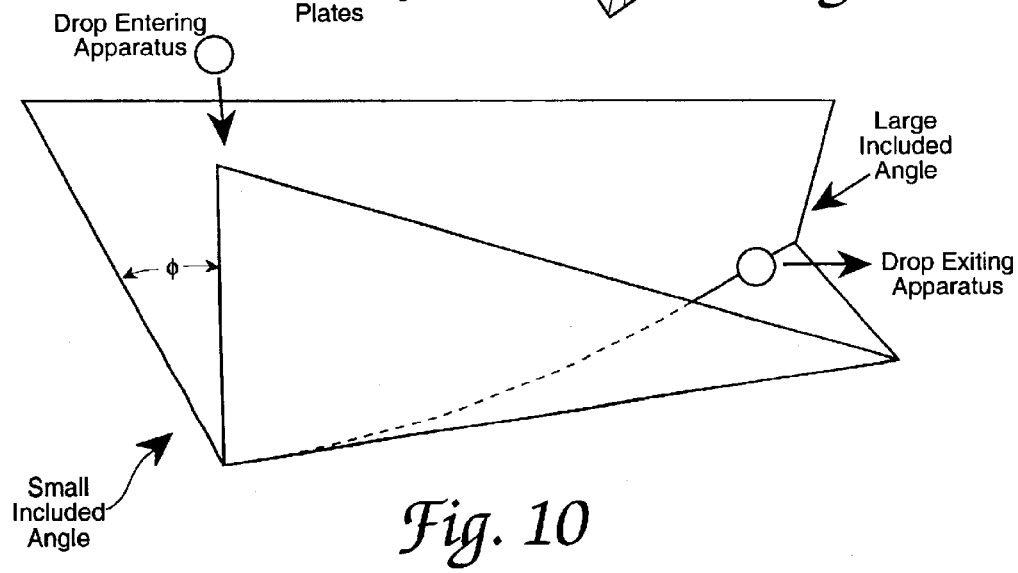
FIG. 10 shows a "folded sheet" determination of contact angle.

As mentioned previously, the apparatus described in Examples 1 and 2 is active in the sense that the plates forming the apex actually move either towards or away from one another during the course of a measurement. This does not however have to be the case. FIG. 10 in the drawings illustrates an apparatus intended to operate in exactly the same manner as the active devices described previously, but now the plates do not move. The FIG. 10 apparatus can best be thought of as a sheet of paper folded in half. Once this fold is accomplished, one end of the folded sheet is opened wide so that the included angle of the folded sheet on that end approaches 180 degrees. The other end of the folded sheet is kept tightly held together, so that its included angle approaches zero degrees. Note that the two sides of the folded sheet do not have to be mirror images of one another. The angle of the apex only has to vary in a known manner.

If, now, a drop of liquid is placed anywhere in the folded sheet, and a force (eg. a mechanical push, a tilt, or a gas jet) is applied to the drop to move it along the folded sheet vertex, at some point the drop will either withdraw from the fold or completely fill it. The point at which this occurs can be determined by the same techniques described for the active apparatus. Likewise, the included angle, $\phi$, at which this occurs can be measured in a variety of ways, the simplest being to measure the external angle of the folded sheet as a function of the distance from the closed end to the open end. Drop removal can be performed in a fashion similar to the active device. This FIG. 10 passive apparatus can also measure dynamic contact angles simply by increasing the speed with which the drop traverses the folded sheet.

EXAMPLE 4

Figure 11:
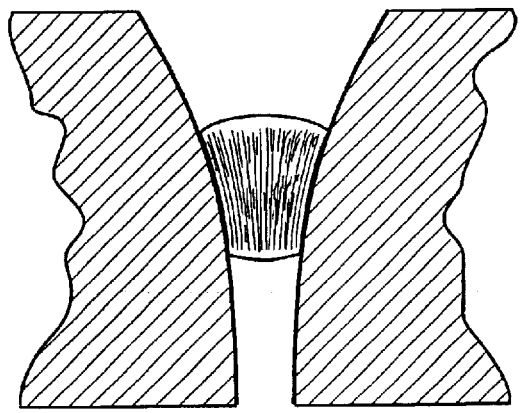
FIG. 11 shows a capillary technique for determination of liquid contact angle.

The present invention's measure of wettability is not limited to the use of "V" shapes formed by plates, but applies to any structure in which the opposing surfaces are not parallel or even symmetrical. Thus, capillaries in which there is a taper, as shown in FIG. 11 of the drawings, or any other change in cross-sectional area, can also be employed to measure the contact angle of a wetting or non-wetting liquid. These capillaries may be fabricated with a variety of tapers that can be constant or variable. They can either be fabricated from the material of interest or coated with the material of interest to determine the transition included angle, $\phi$ and the contact angle, $\theta$, with the desired liquid. A non-wetting liquid may be placed in the large end of the capillary, while a wetting liquid may be exposed to the small end. The FIG. 11 capillary can be used individually or mounted to a small manifold so that several capillaries are exposed to the liquid at the same time.

EXAMPLE 5

Figure 12:
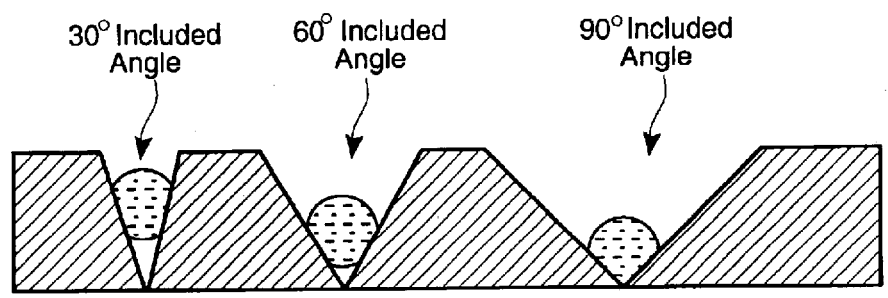
FIG. 12 shows a multiple conical depression technique for liquid contact angle-determination.

One of the least expensive methods to measure contact angle of a liquid is to place a series of conical-shaped depressions having a range of conical angles in a surface to form a conical measuring plate tool. The locations and arrangement of these conical depressions in the plate can be as needed for the specific application. Such a plate will normally contain cones with conical angles that differ by one degree or more. However, for some refined applications the plate may contain cones with conical angles that differ by for example only a tenth of a degree. The side view of a plate with three cones of different angles is shown in FIG. 12 of the drawings herein. In this drawing, the critical included angle, $\phi_{tnw}$, for the non-wetting droplet is represented to be greater than 60° but less than 90°. For the sake of clarity the FIG. 12 cones are shown closed at the bottom so that the shape of all droplets can be observed. The FIG. 12 conical measuring device can be inexpensively produced from the material of interest by, for example, molding or embossing the material surface. Alternatively, the surface of the conical depressions can be coated with the desired material for testing. The thickness of the FIG. 12 conical measuring device is at least in part controlled by the desired depth of the cones which is in turn somewhat related to the materials involved and the expected liquid sample drop size. It should be noted that in place of the cones, multiple rows of angular trenches can be employed in these devices.

Figure 13:
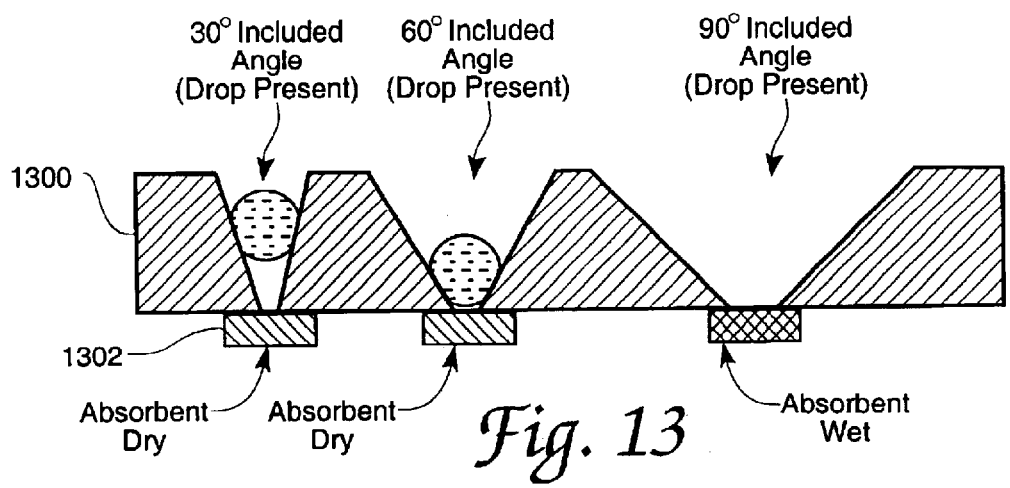
FIG. 13 shows an open bottom and absorbent conical depression technique for liquid contact angle-determination.

FIG. 13 in the drawings shows an alternate arrangement of the FIG. 12 conical measuring device. In the FIG. 13 drawing each cone is truncated leaving a hole in the bottom of the cone and an adsorbent material 1302 is disposed below the truncated cone hole. In order to see if a non-wetting liquid enters a cone with a particular conical angle in FIG. 13, it is only necessary to place a drop of liquid in the cone. If liquid has a $\phi_{tnw}$ less than $\phi$ of the cone, it will go to the bottom of the cone where it will be absorbed by the absorbent material 1302 under the plate leaving the cone empty and the absorbent material in a wetted condition. Alternatively, the presence in the absorbent material of a liquid that has flowed through the conical section can be indicated by the absorbent material in other ways, such as, by a material color change or material electrical conductivity change for examples. To speed up the FIG. 13 process of determining the transitional included angle, it is not necessary to test every conical depression in the measuring device. Rather, an expedient way to utilize an enlarged FIG. 13 conical measurement plate 1300 is to continually bracket the cone having the expected transitional included angle with an ever-decreasing intermediate cones separation.

To use the FIG. 13 conical measuring plate 1300 for wetting liquids, it is only necessary to place the truncated end of the cones (without the absorbent material 1302 of course) in contact with the wetting liquid and observe whether the liquid enters a particular cone. This can be accomplished directly or alternately the small end of each truncated cone can transition into a short capillary (not shown) that becomes the connection to the surface of the plate. This capillary simplifies manufacturing technology and can offer the same diameter entrance for each cone. For a wetting liquid, the plate can be used with the cone in either the upward facing or downward facing orientation. That is, the plate 1300 can be used with the larger end of the cone upward as in the case of non-wetting fluids. In this orientation, the liquid will contact the plate on the bottom. Alternatively, the larger end of the cone can be downward. Liquid will then contact the cone from the top of the plate. For this application the bottom of the cone or capillary can be connected to a small reservoir, which contains the wetting fluid.

Portions of the present invention are described in the technical journal article "Partial Wetting Phenomenon on Nonplanar Surfaces and in Shaped Microchannels" authored by the present inventors and published in the American Chemical Society journal Langmuir 2002, 18, 1225–1230. Publication of this same article occurred on the world-wide-web on Jan. 12, 2002.

Advantage and New Features

Most arrangements used heretofore to measure contact angle require expensive equipment such as goniometer-mounted telescopes. In addition, in order to obtain desirable accuracy expensive computer software is often required. Finally, it is difficult with existing arrangements to accurately measure dynamic contact angles. The present invention enables inexpensive (even throwaway) measuring devices that are quite accurate in measuring contact angle. Several of the devices of the present invention are also capable of easily measuring dynamic contact angles between liquid and solid material surface.

The foregoing description of the preferred embodiment has been presented for purposes of illustration and description. It is not intended to be exhaustive or to limit the invention to the precise form disclosed. Obvious modifications or variations are possible in light of the above teachings. The embodiment was chosen and described to provide the best illustration of the principles of the invention and its practical application to thereby enable one of ordinary skill in the art to utilize the invention in various embodiments and with various modifications as are suited to the particular scope of the invention as determined by the appended claims when interpreted in accordance with the breadth to which they are fairly, legally and equitably entitled.

We claim:

1. A sample transition angle-based method of characterizing the contact angle wetting response of a test liquid on a solid material surface, said method comprising the steps of:
   exposing a sample of said test liquid to a test fixture having a pair of planar segments, including test surfaces of said solid material, disposed in selectable, substantially closed-vertex, angular dispositions;
   said substantially closed-vertex angular dispositions in said test fixture being selectable between angles of zero degrees and one hundred eighty degrees in angular size range;
   changing said test fixture selectable angular disposition, within said zero degrees and one hundred eighty degrees range, until said test liquid sample incurs a transition in test surfaces liquid-solid contact behavior;
   measuring a planar segments angular disposition, within said zero degrees and one hundred eighty degrees selectable range, at which said transition in test surfaces liquid-solid contact behavior occurs; and
   determining, from said planar segments angular measurement and a selected algorithm of planar segments angle and liquid contact angle mathematical relationships, liquid to solid contact angle wetting response characteristics of said applied test liquid sample and said solid material surface.

2. The sample transition angle-based method of characterizing the contact angle wetting response of a test liquid on a solid material test surface of claim 1 wherein said transition in planar segments contact behavior, in said step of changing said test fixture selectable angular disposition, comprises a change in test liquid angular filling of said test fixture substantially closed-vertex.

3. The sample transition angle-based method of characterizing the contact angle wetting response of a test liquid on a solid material test surface of claim 1 wherein said step of changing said test fixture selectable angular disposition, within said zero degrees and one hundred eighty degrees range, comprises changing said test fixture selectable angle disposition until said test liquid sample changes between one of a filled and an empty condition and an empty and a filled condition in an angular interstice region adjacent said substantially closed-vertex.

4. The sample transition angle-based method of characterizing the contact angle wetting response of a test liquid on a solid material surface of claim 1 wherein said step of changing said test fixture selectable angular disposition includes energizing an electric motor connected with said pair of planar segments of said solid material.

5. The sample transition angle-based method of characterizing the contact angle wetting response of a test liquid on a solid material surface of claim 4 wherein said step of energizing an electric motor connected with said pair of planar segments of said solid material includes the steps of:
   energizing a pair of electrical stepping motors each connecting in angular disposition control with one of said pair of planar segments of said solid material; and
   terminating said electrical stepping motors energization in response to change of an electrical signal sensing said planar segments liquid-solid contact angle wetting response.

6. The sample transition angle-based method of characterizing the contact angle wetting response of a test liquid on a solid material test surface of claim 1 wherein said step of changing said test fixture selectable angle disposition until a test liquid sample incurs a transition in test surfaces contact behavior comprises moving at least one of said solid material surfaces until one of an optical and an electrical sample liquid sensor determines said test liquid sample incurs said transition at said test fixture substantially closed-vertex.

7. The sample transition angle-based method of characterizing the contact angle wetting response of a test liquid on a solid material surface of claim 6 wherein said one of an optical and an electrical sensor determining of test liquid sample incurring said transition in planar segments contact behavior is controlling of said changing of said test fixture selectable angle disposition in a closed loop feedback arrangement.

8. The sample transition angle-based method of characterizing the contact angle wetting response of a test liquid on a solid material surface of claim 1 wherein said test liquid sample is non-wetting with respect to said solid material surface, said test liquid sample incurs a transition between an empty and a filled interstice in said substantially closed-vertex angular region, and said selected algorithm of planar segments transition angle to liquid contact angle mathematical relationships comprises a relationship of:

$$\text{liquid contact angle} = [(\tfrac{1}{2})(\text{planar segments transition angle} + 180 \text{ degrees})].$$

9. The sample transition angle-based method of characterizing the contact angle wetting response of a test liquid on a solid material surface of claim 1 wherein said test liquid sample comprises successive drops of said test liquid.

10. The sample transition angle-based method of characterizing the contact angle wetting response of a test liquid on a solid material surface of claim 1 wherein said test liquid sample is wetting with respect to said solid material surface, said test liquid sample comprises a pool of said test liquid, said test liquid sample incurs a transition between a filled interstice and an empty interstice in said substantially closed-vertex angular region, and said selected algorithm of planar segments transition angle to liquid contact angle mathematical relationships comprises a mathematical relationship of:

$$\text{liquid contact angle} = [(\tfrac{1}{2})(180 \text{ degrees} - \text{planar segments transition angle})].$$

11. The liquid transition behavior-based method of determining characteristic angle of contact for a liquid in contact with a solid material surface having fluid-constraining features, said method comprising the steps of:
   measuring an interstice angle of disposition between samples of said solid material at an angle of captured liquid sample transition between interstice-filling and interstice-voiding behavior; and
   computing said characteristic angle of contact for said liquid and said solid material surface using one of a wetting and non-wetting mathematical relationship of:

$$\text{characteristic angle of contact} = [(\tfrac{1}{2})(\text{angle of liquid transition} + 180 \text{ degrees})]$$

and $$\text{characteristic angle of contact} = [(\tfrac{1}{2})(180 \text{ degrees} - \text{angle of liquid transition})].$$

12. The liquid transition behavior-based method of determining characteristic angle of contact for a liquid in contact with a solid material surface having fluid-constraining features of claim 11 wherein said step of measuring an interstice angle of disposition between planar samples of said solid material at an angle of captured liquid sample transition between interstice-filling and interstice-voiding behavior comprises:
- capturing a drop of said liquid sample within a vee shaped and vertex adjacent space of varying but known interstice angular disposition extending lengthwise along a folded paper-like sample of said solid material;
- applying a force to said droplet to move said droplet along said lengthwise vertex until one of responses of a withdrawal and a filling of said vertex by said liquid sample occurs; and
- determining a magnitude of said varying but known interstice angle at a folded paper-like sample location of said withdrawal and filling response.

13. The liquid transition behavior-based method of determining characteristic angle of contact for a liquid in contact with a solid material surface having fluid-constraining features of claim 11 wherein said step of measuring an interstice angle of disposition between samples of said solid material at an angle of captured liquid sample transition includes exposing samples of said liquid to a test fixture having plural interstice angles of disposition arranged in a curving surface disposition.

14. The liquid transition behavior-based method of determining characteristic angle of contact for a liquid in contact with a solid material surface having fluid-constraining features of claim 11 wherein said step of measuring an interstice angle of disposition between samples of said solid material at an angle of captured liquid sample transition includes exposing samples of said liquid to a test fixture having a plurality of surface features with differing interstice angles of disposition.

15. The liquid transition behavior-based method of determining characteristic angle of contact for a liquid in contact with a solid material surface having fluid-constraining features of claim 11 wherein said exposing of samples of said liquid to a test fixture having a plurality of surface features with differing interstice angles of disposition includes absorbing said liquid from an apex region of said surface features.

16. The liquid transition behavior-based method of determining characteristic angle of contact for a liquid in contact with a solid material surface having fluid-constraining features of claim 11 wherein said step of measuring an interstice angle of disposition between samples of said solid material at an angle of captured liquid sample transition between interstice-filling and interstice-voiding behavior includes determining a difference between said interstice-filling and interstice-voiding behavior using one of optical and electrical sensing of interstice liquid presence at said interstice.

17. Liquid to solid material surface contact angle measurement apparatus comprising the combination of:
- a test fixture having a pair of planar segments of said solid material disposed in selectable, substantially closed-vertex, angular dispositions;
- said substantially closed-vertex angular dispositions being selectable between one of an acute angle and an obtuse angle in angular disposition;
- controllable angle adjustment apparatus connected with said solid material planar segments and having both incrementally variable and attained position retention mechanical output characteristics;
- angle measurement apparatus connected with said solid material planar segments and having solid material planar segments measured angle communication capability;
- sample presence detection apparatus responsive to measured angle-determined liquid sample portion presence and absence transitions in an interstice region adjacent said substantially closed-vertex between said solid material planar segments;
- liquid sample communication apparatus disposed in sample introduction relationship with said interstice region adjacent said substantially closed-vertex between said solid material planar segments; and
- mathematical algorithm apparatus inclusive of a plurality of planar segments interstice region liquid sample portion presence and absence measured transition angle, an input variable, to liquid to solid material surface contact angle, an output variable, relationships.

18. The liquid to solid material surface contact angle measurement apparatus of claim 17 wherein said mathematical algorithm apparatus includes a first algorithm relating to non-wetting behavior between said liquid and said solid material surface and a second algorithm relating to wetting behavior between said liquid and said solid material surface.

19. The liquid to solid material surface contact angle measurement apparatus of claim 18 wherein said sample presence detection apparatus responsive to measured angle-determined liquid sample portion presence and absence transitions in an interstice region adjacent said substantially closed-vertex between said solid material planar segments includes one of an optical beam and an electrical current flow based sensing apparatus responsive to said liquid sample portion presence and absence transitions.

20. The liquid to solid material surface contact angle measurement apparatus of claim 19 wherein said controllable angle adjustment apparatus includes an electrical drive motor and a motor control circuit responsive to said one of an optical beam and an electrical current flow based sensing apparatus.

\* \* \* \* \*